United States Patent [19]
Klingenstein

[11] Patent Number: 5,685,321
[45] Date of Patent: Nov. 11, 1997

[54] DEVICE AND METHOD TO FACILITATE COLONOSCOPY BY EXTERNALLY SUPPORTING THE COLON

[76] Inventor: Ralph James Klingenstein, 151 Tremont St., Apt. 23E, Boston, Mass. 02111

[21] Appl. No.: 657,297

[22] Filed: Jun. 3, 1996

[51] Int. Cl.$^6$ .................................................. A61G 15/00
[52] U.S. Cl. ........................ 128/845; 128/876; 602/13; 602/19
[58] Field of Search .................... 128/869, 875, 128/876, DIG. 20, 846, 845; 602/19, 13; 2/44, 311, 318

[56] References Cited

U.S. PATENT DOCUMENTS

| | | | |
|---|---|---|---|
| 3,071,133 | 1/1963 | Eisen | 128/78 |
| 4,120,297 | 10/1978 | Rabischong et al. | 128/78 |
| 4,175,553 | 11/1979 | Rosenberg | 2/44 |
| 4,178,923 | 12/1979 | Curlee | 128/DIG. 20 |
| 4,559,933 | 12/1985 | Batard et al. | 128/78 |
| 4,567,887 | 2/1986 | Couch | 128/DIG. 20 |
| 4,682,587 | 7/1987 | Curlee | 128/DIG. 20 |
| 4,703,750 | 11/1987 | Sebastian et al. | 128/78 |
| 4,836,194 | 6/1989 | Sebastian et al. | 128/78 |
| 5,122,111 | 6/1992 | Sebastian et al. | 602/19 |
| 5,188,585 | 2/1993 | Peters | 602/19 |
| 5,267,948 | 12/1993 | Elliott | 602/19 |
| 5,437,618 | 8/1995 | Sikes | 602/19 |
| 5,450,858 | 9/1995 | Zablotsky et al. | 128/876 |

Primary Examiner—Michael A. Brown
Attorney, Agent, or Firm—Testa, Hurwitz & Thibeault, LLP

[57] ABSTRACT

A medical device, and related method of use, for supporting a patient's colon during a colonoscopy includes a wrap which embraces the patient's abdomen and defines a palpation aperture. The wrap is able to be seemed snugly around the patient's abdomen with a closing mechanism. The wrap includes at least one inflatable bladder which may be inflated to apply to a force to the patient's abdomen, thereby compressing the colon. The palpation aperture exposes a section of the patient's abdomen which allows that section of the patient's abdomen to be palpated during insertion of the colonoscope to verify proper insertion of the scope tip.

19 Claims, 3 Drawing Sheets

DEVICE AND METHOD TO FACILITATE COLONOSCOPY BY EXTERNALLY SUPPORTING THE COLON

FIELD OF THE INVENTION

The present invention relates to an apparatus for facilitating colonoscopy procedures and, in particular, to a medical device for supporting the colon during a colonoscopy by compressing the patient's abdomen and, thus, the underlying colon, particularly the sigmoid colon.

BACKGROUND OF THE INVENTION

The section of the large intestine extending from the rectum to the cecum is referred to as the colon. There are many different medical conditions requiring examination of the lining of the colon. For example, polyps of the colon, while usually asymptomatic, may be accompanied by rectal bleeding, cramps, abdominal pain, or obstruction. Examination of the lining of the colon to determine whether polyps exist is accomplished by performing a total colonoscopy, which is the insertion of a probe through the patient's rectum and into the colon, as shown in FIG. 1A.

The probe generally consists of an imaging device on the end of an elongate, flexible probe member, and may include a device for removing polyps encountered by the colonoscope. It is generally desirable to advance the colonoscope probe completely through the colon until it reaches the cecum.

When performing a colonoscopy, it is often difficult to advance the tip of the colonoscope because some portions of the colon can distend upon further insertion of the probe member, as shown in FIG. 1B. When this occurs, the imaging device on the end of the probe may remain stationary, or actually move backwards, rather than advancing through the colon. In some cases, the colon may expand, especially if the elongate member begins to form a loop inside the colon. This problem is particularly acute in the sigmoid colon because it is not fixed in place, as are other portions of the colon, but rather is loose on a mesentery and therefore tends to be mobile and distend to greater extent than other portions of the colon.

An established solution to this problem is for an endoscopy assistant, or nurse, to compress the abdomen during deep colonoscope insertion in an attempt to support the colon, shown in FIG. 1C. It is especially important to apply pressure to the lower left quadrant of the patient's abdomen in order to support the sigmoid colon, but other areas might also need support during a colonoscopy. Applying pressure to the abdomen helps advance the tip of the elongate member by discouraging the colon from distending as the scope is advanced, either due to direct pressure on the colon or indirect pressure from the organs surrounding the colon. However, this becomes fatiguing and tiring for the assistant and therefore may not be performed correctly, especially during long procedures. Compression of several different locations around the sigmoid colon may have to be tried before the colonoscope can be successfully advanced. Back pain and tendonitis may develop in the assistant, both of which interfere with the efficacy of compression.

Therefore, it is desirable to provide a medical device which allows more consistent application of pressure during colonoscopy in order to speed the examination. It is also desirable to provide a device which would free the endoscopy assistant or nurse to provide other tasks and better monitor the patient.

SUMMARY OF THE INVENTION

These and other advantages are provided by the present invention, which contemplates a method and apparatus for facilitating abdominal compression during a colonoscopy. The invention includes a corset-like wrap which embraces a patient's abdomen to support the patient's colon during a colonoscopy. The wrap includes a closing mechanism which allows the wrap to be secured snugly around the patient's abdomen. The closing mechanism may be a hook and loop closing mechanism, for example, the brand which is commonly known as VELCRO. The wrap also includes one or more inflatable balloons, or bladders, which apply a force to the patient's abdomen and compress the patient's colon when the wrap is secured snugly around the patient's abdomen. The wrap also includes a palpation aperture which exposes at least a portion of the patient's abdomen, typically the right lower quadrant. This allows the endoscopist to palpate the patient's abdomen to examine for transabdominal impression on the cecum and to look for transabdominal transillumination from the cecum. Both of these maneuvers are useful to insure the tip of the colonoscope has reached the cecum, i.e. that the colonoscope has been fully inserted.

In some embodiments, the wrap extends from the patient's ribcage to the pubic symphysis. The wrap may also include a replaceable liner for the side of the wrap which is against the patient during use. This liner may be constructed from a variety thin-walled membrane materials, such as paper or plastic.

In other embodiments, a belt is coupled to the bottom edge of the wrap which secures the bottom edge of the wrap around the patient's abdomen.

The wrap also includes a palpation aperture which leaves at least a portion of the patient's abdomen exposed. In some embodiments the palpation aperture is defined by a separate template which is slideably coupled to the belt. The template can include a fastener which allows it to be fastened to the wrap. In other embodiments, the multiple bladders are inflatable independently of each other and may have different shapes.

In yet another aspect, the invention relates to a method for supporting and compressing a patient's colon during a colonoscopy and involves encompassing the patient's abdomen with a wrap. The wrap includes at least one inflatable bladder and a palpation aperture which exposes the lower right quadrant of the patient's abdomen. The inflatable bladder is inflated in order to apply a force to the patient's abdomen and compress the patient's colon. The exposed portion of the patient's abdomen is palpated to verify proper insertion of the scope. In some embodiments, the wrap includes multiple inflatable bladders which are inflated empirically or in a predetermined sequence. In some embodiments the bladders are superimposed over one another.

BRIEF DESCRIPTION OF THE DRAWINGS

This invention is pointed out with particularity in the appended claims. The above and further advantages of this invention may be better understood by referring to the following description taken in conjunction with the following drawings, in which:

DETAILED DESCRIPTION OF THE INVENTION

Figure 2:
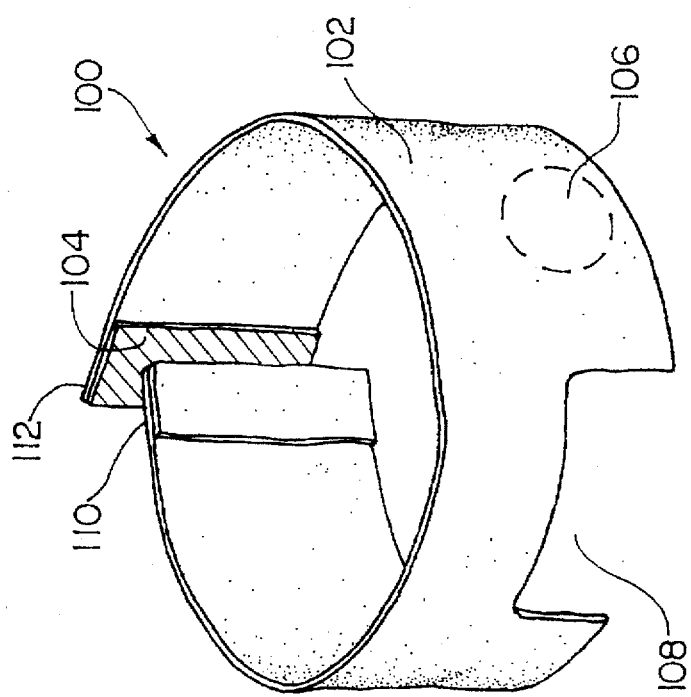
FIG. 2 is a perspective view of an embodiment of the present invention showing only one inflatable bladder.

Referring now to FIG. 2, a therapeutic device 100 for supporting and compressing a patient's colon during a colonoscopy includes a wrap 102 adapted for embracing the patient's abdomen, a closing mechanism 104 coupled to opposite ends of the wrap, and an inflatable bladder 106 associated with the wrap 102. The wrap 102 defines a palpation aperture 108.

The wrap 102 may have a circumferential length between 10 and 80 inches. The width of the wrap 102 should be sufficient to encompass the patient's abdomen from the bottom of the patient's ribcage to the patient's pubic symphysis. Since the wrap 102 is intended to provide some degree of support to the patient's abdomen during the colonoscopy, it is preferred that the wrap 102 be constructed of somewhat inelastic material, such as nylon, cotton, or polyester. Alternatively, the wrap 102 may be constructed from a stiff elastomeric material, such as rubber. The wrap 102 may be made from a composition of materials, for example, the wrap 102 may be primarily fabric having a stiff plastic shell for support. Alternatively, the wrap 102 may be constructed from fabric having structural members interwoven throughout to provide support for the patient's abdomen.

A closing mechanism 104 is coupled to opposite ends 110, 112 of the wrap 102 in order to secure the wrap 102 around the patient's abdomen. Since the desired size of the wrap 102 will vary from patient to patient, it is preferred to provide a closing mechanism 104 which allows the length of the wrap 102 to be adjusted. For example, the closing mechanism 104 may include one or more buckles associated with one or more straps that allow the belt to be shortened or lengthened depending upon the circumference of the patient's abdomen. An acceptable closing mechanism 104 comprises a hook and loop closing mechanism, i.e. the VELCRO brand system. The hook-type fastening member may be coupled at one end 110 of the wrap 102, while the loop-type fastening members are coupled to the other end 112 of the wrap 102 on a side which is opposite the side of the wrap 102 to which the hook-type fasteners are coupled. Whatever closing mechanism 104 is provided, it should be strong enough to secure the opposite ends of the wrap 102 to each other when the wrap 102 is secured snugly around the patient's abdomen.

The inflatable bladder 106 is coupled to the wrap 102 at a location which places the inflatable bladder 106 over the area of the patient's abdomen that is to be compressed. For colonoscopy applications, this is generally the lower left quadrant of the patient's abdomen. Other applications may require compression of different sections of the patient's abdomen or colon. Compression of the abdomen is accomplished by inflating the bladder 106. The bladder 106 may be placed advantageously on the wrap 102 so that it covers the lower left hand quadrant of the patient's abdomen. This placement of the inflatable bladder 106 allows the sigmoid colon to be supported during a colonoscopy.

Inflatable bladder 106 may be coupled to the wrap 102 in any manner, so long as the bladder 106 material retains its integrity. For example, bladder 106 may be provided with an additional flap of material which is stitched to the wrap 102. Alternatively, bladder 106 may be coupled to the wrap 102 using a hook and loop fastening mechanism, which allows the bladder to be repositioned to accommodate the differing physiques of individual patients.

Figure 1C:
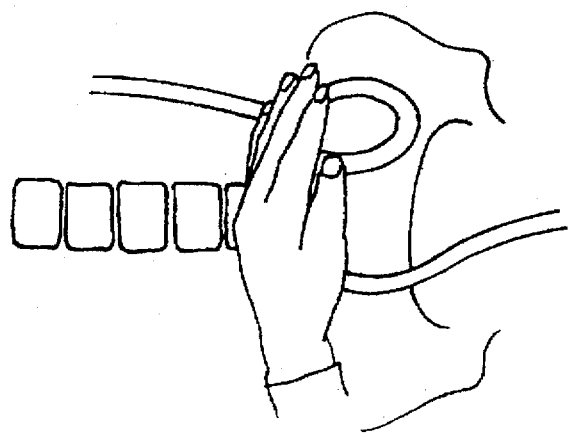
FIG. 1C is a from view of an endoscopy assistant applying pressure to the sigmoid colon to aid in the colonoscope probe's advancement through the sigmoid colon.
Figure 1B:
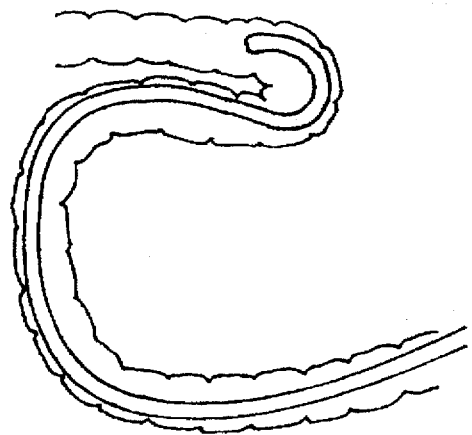
FIG. 1B is a front view of a colonoscopy being performed in the sigmoid colon showing the colon distending.
Figure 1A:
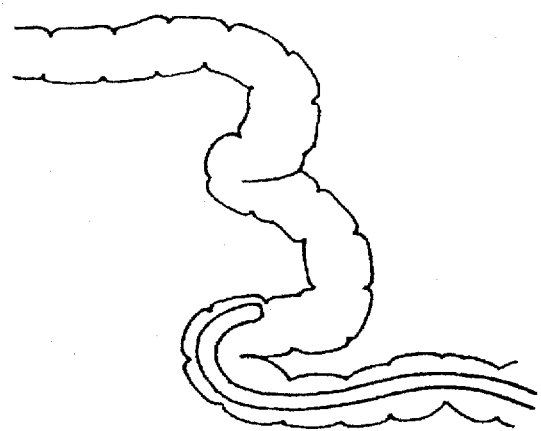
FIG. 1A is a from view of a colonoscopy being performed in the sigmoid colon.
Figure 3A:
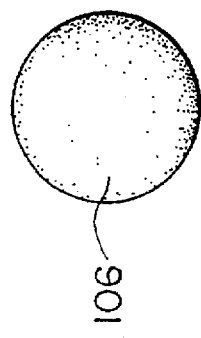
FIG. 3A is a top view of an embodiment of an inflatable bladder.
Figure 3B:
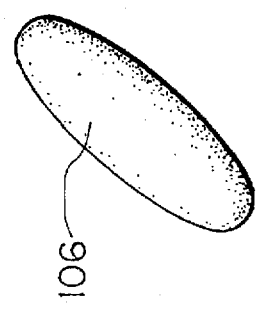
FIG. 3B is a top view of an embodiment of an inflatable bladder.
Figure 3C:
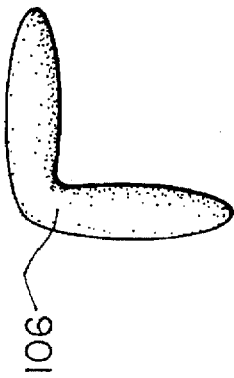
FIG. 3C is a top view of embodiment of an inflatable bladder.

Compression of the patient's abdomen and support of the appropriate section of the patient's colon may require different patterns of compression at different times due to the particular application for which the device is used, or to account for individual variations in physiques. To accommodate variations in patient physique, more than one inflatable bladder 106, or inflatable bladders 106 having different shapes may be provided. FIG. 3A depicts a round inflatable bidder 106. FIG. 3B shows an oblong inflatable bladder 106. FIG. 3C shows an L-shaped inflatable bladder 106. Differently shaped bladders 106 apply different compression forces to the patient's abdomen when they are inflated. Other bladder shapes will be apparent to those skilled in the art.

Figure 4:
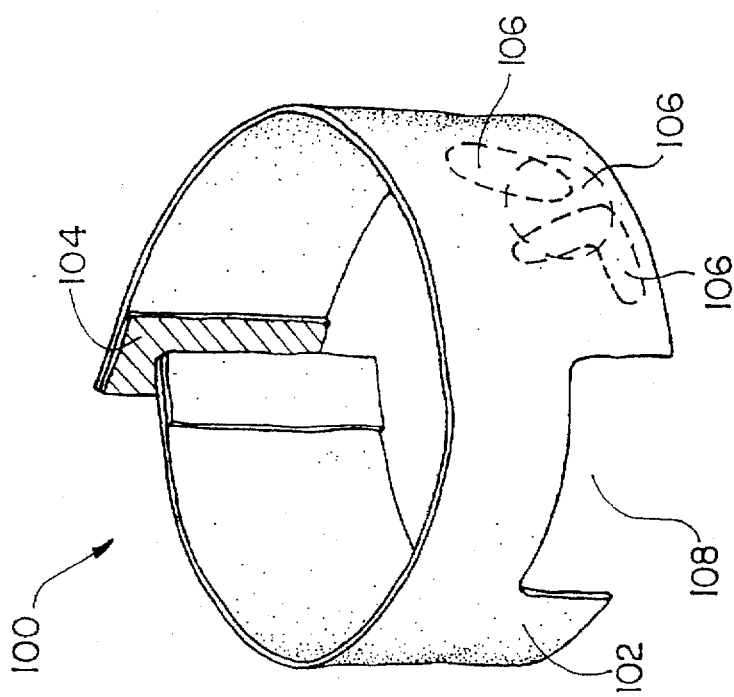
FIG. 4 is a perspective view of an embodiment of the present invention including multiple inflatable bladders.

A wrap 102 may be provided with one of these differently shaped bladders, in which case the bladder may be removeably coupled to the wrap 102 so that different bladders 106 may be easily coupled and uncoupled to configure the wrap 102 for different procedures. FIG. 4 shows an embodiment in which multiple inflatable bladders 106 are simultaneously coupled to a wrap 102. The bladders 106 may be inflated in succession without removing the wrap 102 from the patient's abdomen, thereby allowing different compression patterns to be used while performing the colonoscopy. If necessary, all bladders may be simultaneously inflated.

For embodiments in which multiple inflatable bladders 106 are provided, the bladders 106 may be inflated empirically or in a predetermined sequence during the procedure. Selection of which inflatable bladder 106 to inflate may be made by a switch, or multiple valves may be provided on the wrap 102 corresponding to, and in fluid communication with, each of the inflatable bladders 106. Inflation of the bladders 106 may be accomplished by a variety of means known in the art, including a foot pedal pump or squeeze bulb attached to the bladder 106 by a hose, or by electric air pump.

The inflatable bladders 106 may be constructed from any material known to be useful for manufacturing inflatable devices. It is desirable that, since the inflatable bladder 106 is placed against the patient's abdomen, the inflatable bladder 106 be constructed from a material which allows for easy cleaning and sterilization. For example, the inflatable bladder 106 may be manufactured from plastic, nylon, rubber, or a plastic/nylon blend. In some embodiments the bladder 106 may be manufactured from an elastomeric material. Inflatable bladder 106 may be made by any process known in the art and may be constructed from one unitary template of material or multiple, separate pieces of material.

The palpation aperture 108 may be defined by the wrap 102 anywhere along its length, provided that the aperture 108 exposes the lower right quadrant of a patient's abdomen when the wrap 102 is secured around the patient. The lower right quadrant of a patient's abdomen is approximately defined by drawing a horizontal and a vertical line which intersect at the patient's navel. The portion of the abdomen below the horizontal line and to the right of the vertical line is the lower right quadrant of the patient's abdomen. The palpation aperture should expose this entire quadrant in order to allow the endoscopist to palpate the patient's abdomen and examine it for transabdominal impression on the cecum or transabdominal transillumination from the cecum.

The proper size for a palpation aperture 108 will vary among individual patients. Appropriately-sized palpation apertures 108 may be furnished by providing differently-sized wraps 102; each wrap 102 intended for use only on a certain range of abdomen circumferences. This allows the palpation aperture 108 to accommodate a wide range of physiques without impairing the stiffness of the wrap 102. The wrap 102 may be provided with additional support surrounding the palpation aperture 108, such as plastic ribs which support the perimeter of the palpation aperture 108.

In some embodiments, a liner is coupled to the side of the wrap 102 which is adjacent the patient's abdomen when the wrap 102 is secured around the patient. The liner may be coupled to the wrap by a variety of well-known coupling means, including snaps, clips, and hook and loop fastening mechanisms. The liner may be used primarily for sanitary purposes, in which case a new liner is coupled to the wrap 102 for each new patient. In this case, the liner may be manufactured from plastic or paper which has a plastic backing. Alternatively, the liner may be used to provide a level of comfort during the procedure, in which case, the liner may be made from any material having some degree of compression, for example, foam rubber.

Alternatively, the liner may used separately from the wrap 102. For example, the liner, which may be constructed from any of the materials described above, can be placed on the patient's abdomen before the wrap 102 is secured around the patient. In this case, the liner should be shaped appropriately so that the palpation aperture 108 is not blocked by the liner. This may be accomplished by providing the liner with an aperture corresponding to the palpation aperture 108 of the wrap 102. Alternatively, the liner may be manufactured of easily tearable material, and a the portion of the liner extending into the palpation aperture 108 is simply ripped off. In these embodiments, the liner may be perforated to aid in ripping it.

The wrap 102 supports and compresses a patient's colon during a colonoscopy. The wrap 102 encompasses the patient's abdomen snugly, but not tightly, and may be secured around the patient's abdomen by using the closing mechanism 104. The inflatable bladder 106 is inflated to apply pressure to the patient's abdomen at a predetermined point. Inflatable bladder 106 may be inflated after the wrap 102 is secured around the patient's abdomen or it may inflated before the wrap is secured around the patient's abdomen.

For embodiments in which multiple inflatable bladders 106 are provided the bladders 106 may be inflated in a predetermined sequence during the procedure to apply different patterns of compression to the patient's abdomen and aid in advancement of the colonoscopy tip. Alternatively, a first inflatable bladder 106 may be inflated to apply a first pattern of compression to the patient's abdomen and, if the tip of the colonoscope is unable to be advanced, the first inflatable bladder 106 is deflated and a second, differently-shaped bladder 106 is inflated to provide for a different pattern of compression to the patient's abdomen. Selection of the inflatable bladder 106 to inflate may be made by a switch, or multiple valves may be provided on the wrap 102 which corresponds to each of the inflatable bladders 106. Inflation of the bladders 106 may be accomplished by any means known in the art, including a foot pedal pump attached to the bladder 106 by a hose.

The palpation aperture 108 defined by the belt allows the patient's abdomen to be palpated to determine if the colonoscope tip has reached the end of the colon. This may be done by examining for transabdominal impression of the colonoscope tip on the cecum or examining the abdomen for transabdominal transillumination from the cecum. Determination that insertion of additional colonoscope is not resulting in the advancement of the colonoscope tip through the colon suggests that a different compression should be attempted in order to allow the tip to advance to the cecum.

Figure 5:
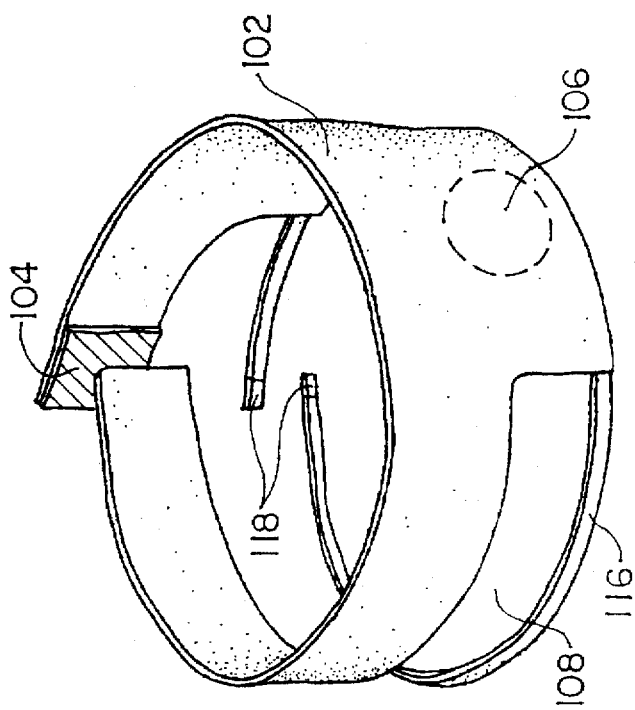
FIG. 5 is a perspective view of an embodiment of the present invention which includes a belt for securing the bottom of the wrap around the patient's abdomen.

FIG. 5 shows another embodiment of the present invention. In this embodiment, a wrap 102 is provided with a closing mechanism 104 on opposite ends of the wrap 102. The closing mechanism 104 secures the top edge 112 of the wrap 102 snugly around the patient's abdomen.

The wrap 102 is provided with one or more inflatable bladders 106 (shown in phantom view in FIG. 5), which are manufactured and positioned as described above. The bottom edge 114 of the wrap 102 is secured around the patient's abdomen with a belt 116. The belt is coupled to the bottom edge 114 of the wrap 102 in any fashion known in the art. For example, the belt 116 may be surrounded by a sleeve of the wrap's 102 material. Alternatively, the belt 116 may be sewn to the bottom edge 114 of the wrap 102.

The belt 116 is also secured by way of a closing mechanism 118 which is disposed on opposite sides of the belt 116. As above, in order to accommodate various physiques, the closing mechanism 118 should allow the circumference of the belt 116 to be adjusted. Closing mechanism 118 may be buckles, a hook and loop closing mechanism, or the belt 116 may simply tie around the patient's abdomen.

Figure 6:
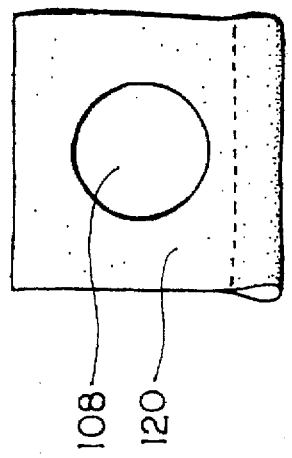
FIG. 6 is a top plan view of a template for providing a palpation aperture.

As shown in FIG. 5, the palpation aperture 108 in this embodiment is roughly defined by the wrap 102 and the belt 116. This embodiment allows the device to be used on a wide range of patients since the aperture 108 defined by the wrap 102 is potentially very large. However, in many applications it may be desirable to reduce the size of the palpation aperture 108 and increase the stiffness of the wrap. For these applications, a template 120 may be provided, shown in FIG. 6, which defines a palpation aperture 108.

The template 120 may be coupled to the wrap 102 by, for example, a hook and loop fastener. In some embodiments, the template 120 is disposed over the patient's abdomen such that the desired area of the patient's abdomen is exposed. The wrap 102 is then disposed over the template 120 and fastened to it. In these embodiments, the template 120 is provided with the hook portion of the fastener while the wrap 102 is provided with the hook portion of the fastener in order to increase patient comfort. Once the wrap 102 is fastened to the template 120, the wrap 102 is secured around the patient's abdomen. This provides additional support for the edge of the wrap 102 as well allowing the device 100 to be used on a wide range of physiques.

In another embodiment, the template 120 has a sleeve along its bottom edge and one half of a hook and loop fastener. In this embodiment, the palpation aperture 108 may be positioned at any point along the wrap 102 by sliding the template 120 along the belt 116 until the template 120 is in the desired position, and pressing the template 120 against the wrap 102 to engage the hook and loop fastener. In this embodiment, the template is provided with the loop portion of the hook and loop fastener to increase patient comfort. The template 120 may be coupled to the belt 116 by stitching the template 120 to the belt 116, although it is preferred to provide the template 120 with a sleeve along its bottom edge through which the belt 116 may pass.

The template 120 may be made of the same material as the wrap 102, i.e. cotton, nylon, or any blend of natural or synthetic fibers. The template 120 should be strong and durable enough to be reused many times. The edges of the template 120 may be reinforced, for example, by additional stitching.

Although certain preferred embodiments are specifically illustrated and described herein, it will be appreciated that many other modifications and variations of the present invention are possible in light of the above teachings and within the purview of the appended claims without departing from the spirit and intended scope of the invention. Other objects, features, and advantages of the invention shall become apparent when the following drawings, description, and claims are considered.

What is claimed is:

1. A therapeutic device for supporting the colon during a colonoscopy, said device comprising:

a wrap of predetermined length adapted for embracing a patient's abdomen, said wrap having an outer surface and an inner surface and defining a palpation aperture, wherein said inner surface corresponds to the surface of said wrap which is adjacent the patient when the wrap embraces the patient's abdomen;

and an inflatable bladder disposed against said inner surface of said wrap such that, when said wrap is secured around the patient's abdomen, inflation of said bladder applies a force to said inner surface of said wrap and to the left side of the patient's abdomen, said palpation aperture being disposed along the length of said wrap with respect to said bladder so as to expose the patient's lower right abdomen for palpation.

2. The device of claim 1 wherein said wrap is constructed to have a width such that said wrap extends from the patient's rib cage to the patient's pubic symphysis.

3. The device of claim 1 further comprising a replaceable liner for said inner surface of said wrap.

4. The device of claim 3 wherein said liner is constructed of paper.

5. The device of claim 3 wherein said liner is constructed of plastic.

6. The device of claim 1 further comprising a closing mechanism coupled to opposite ends of said wrap for securing said wrap around the patient's abdomen.

7. The device of claim 1 further comprising a plurality of inflatable bladders associated with said wrap.

8. The device of claim 7 wherein said plurality of inflatable bladders has different shapes.

9. The device of claim 7 wherein each of said plurality of inflatable bladders overlaps the other bladders in the plurality.

10. The device of claim 7 wherein said plurality of inflatable bladders are associated with said wrap at a point along its length such that, when said wrap is secured around the patient's abdomen, inflation of said plurality of inflatable bladders applies forces to said inner surface of said wrap and to the lower left side of the patient's abdomen.

11. A therapeutic device for supporting a patient's colon during a colonoscopy, said device comprising:

a wrap of predetermined length adapted for embracing a patient's abdomen, said wrap having an outer surface and an inner surface and defining a palpation aperture, wherein said inner surface corresponds to the surface of said wrap which is adjacent the patient when the wrap embraces the patient's abdomen;

an inflatable bladder disposed against said wrap such that, when said wrap is secured around the patient's abdomen, inflation of said bladder applies a force to said inner surface of said wrap and the lower left side of the patient's abdomen; and a belt having a length sufficient to encompass a patient's abdomen and coupled to said bottom edge of said wrap for securing the bottom edge of said wrap around the patient's abdomen.

12. The device of claim 11 wherein said palpation aperture is defined by a template which is slideably coupled to said belt, said template including a hook and loop connection mechanism for coupling said aperture to said wrap.

13. The device of claim 11 further comprising a plurality of inflatable bladders associated with said wrap.

14. The device of claim 13 wherein each of said plurality of inflatable bladders is inflatable independently of the other of said plurality of inflatable bladders.

15. The device of claim 13 wherein said plurality of inflatable bladders include a round bladder, an oblong bladder, and an irregular bladder.

16. A method for supporting a patient's colon during a colonoscopy, said method comprising the steps of:

(a) encompassing the patient's abdomen with a wrap having an inflatable bladder and defining a palpation aperture which exposes the lower right quadrant of the patient's abdomen;

(b) inflating said inflatable bladder to apply a force to the patient's abdomen; and (c) palpating the portion of the patient's abdomen exposed by said palpation aperture to verify proper insertion of the scope.

17. The method of claim 16 wherein step (a) further comprises encompassing the patient's abdomen with a wrap having a plurality of inflatable bladders and defining a palpation aperture which exposes the lower right quadrant of the patient's abdomen.

18. The method of claim 17 wherein step (b) further comprises inflating each of said plurality of inflatable bladders in a predetermined sequence.

19. The method of claim 16 further comprising the step of securing said wrap around the patient's abdomen between step (a) and step (b).

* * * * *